United States Patent
Salah et al.

(10) Patent No.: US 12,109,088 B2
(45) Date of Patent: Oct. 8, 2024

(54) METHOD OF EVALUATING AN ORTHODONTIC APPLIANCE

(71) Applicant: DENTAL MONITORING, Paris (FR)

(72) Inventors: Philippe Salah, Bagnolet (FR);
Thomas Pellissard, Clichy (FR);
Guillaume Ghyselinck, Cantin (FR);
Laurent Debraux, Paris (FR)

(73) Assignee: DENTAL MONITORING, Paris (FR)

( * ) Notice: Subject to any disclaimer, the term of this patent is extended or adjusted under 35 U.S.C. 154(b) by 512 days.

(21) Appl. No.: 17/395,160

(22) Filed: Aug. 5, 2021

(65) Prior Publication Data
US 2021/0361387 A1    Nov. 25, 2021

Related U.S. Application Data

(63) Continuation-in-part of application No. 16/001,049, filed on Jun. 6, 2018, now Pat. No. 11,109,945.

(30) Foreign Application Priority Data

Jun. 9, 2017    (FR) ..................................... 1755187

(51) Int. Cl.
*A61C 7/00*        (2006.01)
*A61C 7/08*        (2006.01)
(Continued)

(52) U.S. Cl.
CPC .............. *A61C 7/002* (2013.01); *A61C 9/004* (2013.01); *A61C 7/08* (2013.01); *A61C 7/10* (2013.01); *A61C 7/12* (2013.01)

(58) Field of Classification Search
CPC ........... A61C 7/002; A61C 9/004; A61C 7/08; A61C 7/10; A61C 7/12; G16H 20/40; G16H 30/40
(Continued)

(56) References Cited

U.S. PATENT DOCUMENTS 8,562,338 B2 * 10/2013 Kitching .................. A61C 7/08
                                                433/24
10,248,883 B2 * 4/2019 Borovinskih ............. G06T 7/32
(Continued)

FOREIGN PATENT DOCUMENTS

EP        3410443 A1 * 12/2018    ............. A61C 7/002
EP        3213293 B1 *  9/2021    ....... A61B 1/000094
(Continued)

OTHER PUBLICATIONS

International Search Report and Written Opinion from Corresponding International Application No. PCT/EP2022/072150, dated Jan. 10, 2023, 20 pages.

*Primary Examiner* — Mahendra R Patel
(74) *Attorney, Agent, or Firm* — Ronald M. Kachmarik; Cooper Legal Group LLC (57) ABSTRACT

A method for evaluating an orthodontic appliance. Acquisition of a two-dimensional "appliance image" of teeth at least partially representing the orthodontic appliance in a service position. Acquisition of a two-dimensional "dentition image" of the teeth. If a determination of comparable dental and appliance attributes is not possible from the appliance image and from the dentition image, respectively, conversion of the appliance image and/or of the dentition image so that the appliance image be compatible with the dentition image. Determination of dental and appliance attributes relative to the shape of the tooth represented on the dentition image and relative to the shape of the orthodontic appliance on the appliance image. Comparison of the dental and appliance attributes, followed by determination of at least one score. At least one image is acquired with a mobile phone.

17 Claims, 5 Drawing Sheets

(51) Int. Cl.
*A61C 7/10* (2006.01)
*A61C 7/12* (2006.01)
*A61C 9/00* (2006.01)

(58) Field of Classification Search
USPC .......................................................... 382/128
See application file for complete search history.

(56) References Cited

U.S. PATENT DOCUMENTS

| | | | |
|---|---|---|---|
| 10,390,904 B2 * | 8/2019 | Bindayel | A61C 7/002 |
| 10,548,690 B2 * | 2/2020 | Wen | A61C 7/002 |
| 10,806,376 B2 * | 10/2020 | Lotan | A61C 7/002 |
| 2007/0134613 A1 * | 6/2007 | Kuo | G06T 19/00 |
| | | | 433/24 |
| 2009/0191503 A1 * | 7/2009 | Matov | A61C 7/16 |
| | | | 433/2 |
| 2010/0068672 A1 * | 3/2010 | Arjomand | A61C 7/00 |
| | | | 433/24 |
| 2013/0323665 A1 * | 12/2013 | Dinh | A61C 7/08 |
| | | | 427/2.29 |
| 2015/0257856 A1 * | 9/2015 | Martz | A61C 7/145 |
| | | | 433/6 |
| 2016/0128803 A1 * | 5/2016 | Webber | A61C 7/36 |
| | | | 264/16 |
| 2017/0065372 A1 * | 3/2017 | Mah | A61N 5/0601 |
| 2017/0100214 A1 * | 4/2017 | Wen | G16H 30/20 |
| 2017/0128168 A1 * | 5/2017 | Bindayel | A61C 7/14 |
| 2017/0251954 A1 * | 9/2017 | Lotan | A61B 5/0088 |
| 2018/0078334 A1 | 3/2018 | Lotan et al. | |
| 2018/0344430 A1 | 12/2018 | Salah et al. | |
| 2019/0125493 A1 * | 5/2019 | Salah | A61C 7/002 |
| 2020/0360111 A1 | 11/2020 | Salah et al. | |

FOREIGN PATENT DOCUMENTS

| | | | | |
|---|---|---|---|---|
| FR | 2977469 A1 * | 1/2013 | ....... | A61B 1/000094 |
| FR | 3027504 A1 * | 4/2016 | ....... | A61B 1/000094 |
| JP | 2012179370 A * | 9/2012 | ....... | A61C 7/00 |
| WO | WO-2011118839 A1 * | 9/2011 | ....... | A61B 6/145 |
| WO | WO-2017144652 A1 * | 8/2017 | ....... | A61C 19/05 |
| WO | 2021/030284 A1 | 2/2021 | | |

* cited by examiner

METHOD OF EVALUATING AN ORTHODONTIC APPLIANCE

TECHNICAL FIELD

The present invention relates to a method of evaluating orthodontic appliance and more particularly evaluating the shape of a tray-like orthodontic appliance known as an "aligner", worn by a patient, particularly so as to evaluate how well the shape of the orthodontic aligner conforms to the positioning of the teeth of said patient. The invention also relates to a method for adapting a treatment using orthodontic aligners.

The invention finally relates to a computer program for implementing these methods.

PRIOR ART

Conventionally, at the start of orthodontic treatment, the orthodontist determines the positioning of the teeth, referred to as the "set-up", that he wishes to obtain at the end of the treatment. The set-up may be defined by means of an impression or from a three-dimensional scan of the teeth of the patient. The orthodontist then accordingly manufactures an orthodontic appliance suited to this treatment.

The orthodontic appliance may be a tray-like device known as an aligner. An aligner conventionally comes in the form of a removable monobloc appliance, conventionally made of a transparent polymer, which comprises a tray shaped in such a way that several teeth of a dental arch, generally all the teeth of an arch, can be housed therein.

The shape of the aligner is tailored to hold the aligner in position on the teeth while at the same time applying an action towards correcting the positioning of certain teeth.

The shapes that the various aligners at various stages in the treatment need to adopt are conventionally determined at the start of the treatment, then all of the corresponding aligners are manufactured. At predetermined moments, the patient changes aligner.

Treatment using aligners is advantageously less of a burden on the patient. In particular, the number of orthodontist appointments is limited. Furthermore, the pain is less than with a metal orthodontic arch wire attached to the teeth.

The market for orthodontic aligners is therefore growing.

At regular intervals, the patient visits the orthodontist for a visual inspection, notably to check whether the movement of the teeth meets expectations and whether the aligner being worn by the patient is still suitable for the treatment.

If the orthodontist diagnoses that the treatment is inappropriate, he takes a new impression of the teeth, or as is equivalent, a new three-dimensional scan of the teeth, then orders a new series of aligners configured accordingly. It is reckoned that, on average, the number of aligners ultimately manufactured is around 45, rather than the 20 aligners conventionally intended at the start of the treatment.

The need to travel to the orthodontist's is a burden on the patient. The patient's confidence in his orthodontist may also be undermined. The unsuitability may be in aesthetic. Finally, this results in additional expense.

The number of orthodontist check-ups needs therefore to be limited.

There is a need for solutions that remedy these problems.

One object of the invention is to provide an at least partial response to this need.

SUMMARY OF THE INVENTION

The invention provides a method for evaluating the shape of an orthodontic aligner worn by a patient, said method comprising the following steps:

1) acquisition of at least one two-dimensional image of the teeth of said patient, referred to as "updated image", under actual acquisition conditions;
   at least one updated image referred to as "aligner image", at least partially representing the aligner in a service position in which it is worn by said teeth; and at least one updated image referred to as "dentition image", identical to or different from the aligner image, representing said teeth,
2) if the dentition image is different from the aligner image, conversion of the dentition image so that it represents said teeth (represented on the dentition image) as seen under the acquisition conditions used during the acquisition of the aligner image in step 1);
3) determination, for each of a plurality of teeth represented on the dentition and aligner images, of interior and exterior tooth outlines representing the outline of the free end of said tooth on the dentition and aligner images, respectively;
4) comparison of the interior and exterior tooth outlines, followed by determination of at least one score according to said comparison.

As will be seen in greater detail in what follows of the description, a method according to the invention makes it considerably easier to evaluate the suitability of the aligner for the treatment, while at the same time making this evaluation particularly reliable. In particular, the method can be implemented using simple photographs or films, taken without special precaution, for example by the patient. The number of orthodontist appointments can therefore be limited.

For preference, an evaluation method according to the invention also has one or more of the following optional features:

the method comprises, after step 4), the following step:
5) comparison of the score against an acceptability threshold and the emission of information according to the result of the comparison;
the dentition and aligner images are different and the method comprises the following steps:
   (a) prior to step 1) for preference at the start of the treatment or before the start of the treatment, the creation of a digital three-dimensional model of at least part of a dental arch bearing said teeth, or "initial reference model" and, for each tooth of the initial reference model, definition of a digital three-dimensional reference model of said tooth, or "tooth model";
   (b) modification of the initial reference model by moving the tooth models until a final reference model compatible with the dentition image is obtained;
   (c) search for a two-dimensional view of the final reference model that is compatible with the aligner image;
   (d) conversion of the dentition image into said view;
alternatively, said dentition and aligner images are one and the same image;
step 4) comprises the following steps:
for each of a plurality of teeth for which the interior and exterior tooth outlines have been determined;
   i) determination of a distance between the interior and exterior tooth outlines;
   ii) determination of a distance threshold, preferably using the distances determined in step i);
   iii) for each of said teeth, determination of a distance score dependent on the distance between the interior and exterior tooth outlines, and the distance threshold;

said distances are measured in pixels;

in step ii), the distance threshold is dependent on the smallest of the distances determined in step i);

alternatively, step 4) comprises the following steps:

i') for each pair of an adjacent left-hand tooth and of an adjacent right-hand tooth in at least one triplet of adjacent first, second and third teeth, for each of which interior and exterior tooth outlines have been determined, the first and third teeth being adjacent to the second tooth, determination of an offset between the interior teeth outline of said left-hand tooth and the interior teeth outline of said right-hand tooth, referred to as "interior offset", and determination of an offset between the exterior teeth outline of said left-hand tooth and the exterior teeth outline of said right-hand tooth, referred to as "exterior offset", then determination of the difference between the interior offset and the exterior offset, known as the "offset difference";

ii') determination of an offset-difference threshold, preferably using the offset differences determined in step i');

iii') determination, for at least one, preferably for each, tooth of said triplet, of at least one offset score, dependent on the offset difference with an adjacent tooth, and on the offset-difference threshold;

the interior and exterior offsets are measured in pixels;

in step iii'), the offset-difference threshold is dependent on the smallest of the offset differences determined in step i').

The invention also relates to a method of adapting an orthodontic treatment, in which method an evaluation method according to the invention is implemented and then, according to the result of said evaluation, a new aligner is manufactured.

The invention also relates to:

a computer program and, in particular, a specialist application for a mobile telephone, comprising program code instructions for executing one or more, preferably all, of steps 1) to 4), preferably 1) to 5), when said program is run by a computer, a computer medium on which such a program is recorded, for example a memory or a CD-ROM; and a personal device, in particular a mobile phone or a tablet, on which such a program is loaded.

The invention also relates to a system comprising:

a three-dimensional scanner able to implement step (a) described hereinbelow, and a personal device, preferably a mobile telephone, loaded with a program according to the invention.

DEFINITIONS

A "dentition" is understood to mean a set of teeth.

A "patient" is understood to mean any person for whom a method according to the invention is implemented, whether this person is sick or not.

By "dental care professional" what is meant is any person or company qualified to provide dental care, which in particular includes a manufacturer of orthodontic appliances such as aligners, an orthodontist and a dentist.

An "orthodontic appliance" may be of any known type. In particular, it may be active or passive. It may be, for instance, an aligner or an appliance comprising brackets and an arch, usually a metallic wire, fixed on the brackets. A bracket, a button or an attachment fixed on a tooth are also regarded as orthodontic appliances.

The "acquisition conditions" specify the position and orientation in space of an image acquisition apparatus relative to the patient's teeth (actual acquisition conditions) or to a three-dimensional model of the teeth of the patient (virtual acquisition conditions), and preferably the calibration of this image acquisition apparatus, and notably the values of aperture, exposure time, focal length and sensitivity. Acquisition conditions are said to be "virtual", or "theoretical", when they correspond to a simulation in which the acquisition apparatus would be under said acquisition conditions (theoretical positioning and preferably virtual calibration of the acquisition apparatus).

A 3-D scanner is an apparatus that makes it possible to obtain a three-dimensional representation of an object.

What is meant by an "image" is a two-dimensional image such as a photograph. An image is made up of pixels.

A "tooth model" is a digital three-dimensional model of a tooth. As an exception to this definition, in an embodiment of steps (a') to (d') described hereafter for the detection of the removal of an orthodontic appliance, an "enriched tooth model" is a digital three-dimensional model of a tooth and of an orthodontic appliance directly fixed on said tooth, such as a bracket, a button or an attachment.

A three-dimensional digital model of a set of teeth of a patient is "compatible" with an image when there is a view of this model that corresponds to said image, that is to say such that the elements of said model, for example the outlines of the tooth models, are positioned, relative to one another, like the actual elements that they are modeling, for example the outlines of said teeth, on said image. Thus, a final reference model is compatible with a dentition image if a view of the final reference model allows for the outlines of the tooth models to be viewed in such a way as to make them superposable on the outlines of said teeth on said dentition image.

Said view may be observed by a virtual image acquisition device, under virtual acquisition conditions that may also be qualified as being "compatible" with the image.

When a three-dimensional digital model is compatible with an image, the positioning of the tooth models in this model is also qualified as being "compatible" with the image.

An appliance image is "compatible" with a dentition image if the outlines of the teeth represented on both the appliance image and on the dentition image are superposable.

The "service position" is the position in which the aligner is worn by the patient.

An "outline" of an object is a line displaying, completely or partly, the shape of said object on an image. In an embodiment, a point of this line may be regarded as an "outline".

The terms "comprise", "include" or "have" should be interpreted broadly and without limitation, unless specified otherwise.

BRIEF DESCRIPTION OF THE FIGURES

Additional features and advantages of the invention will become further apparent upon reading the following detailed description and from studying the attached drawing, in which:

FIG. 10 schematically depicts step 2) of a method according to the invention, FIG. 11 schematically depicts part of a dental arch bearing an orthodontic appliance comprising an arch and brackets, FIG. 12 schematically depicts a dental arch bearing a palatal expander appliance.

DETAILED DESCRIPTION

Figure 1:
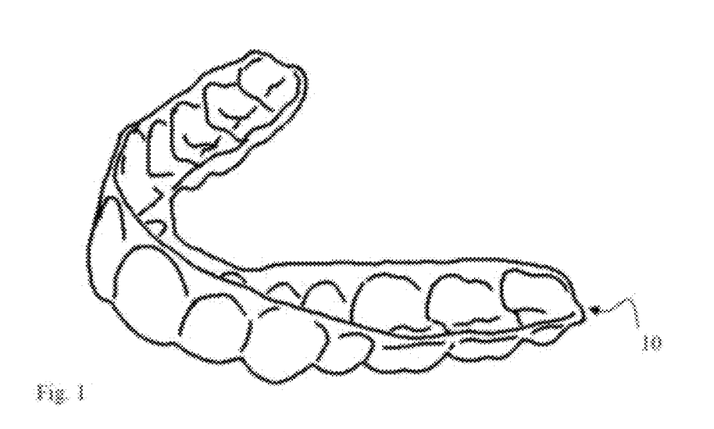
FIGS. 1 and 2 depict an orthodontic aligner.
Figure 2:
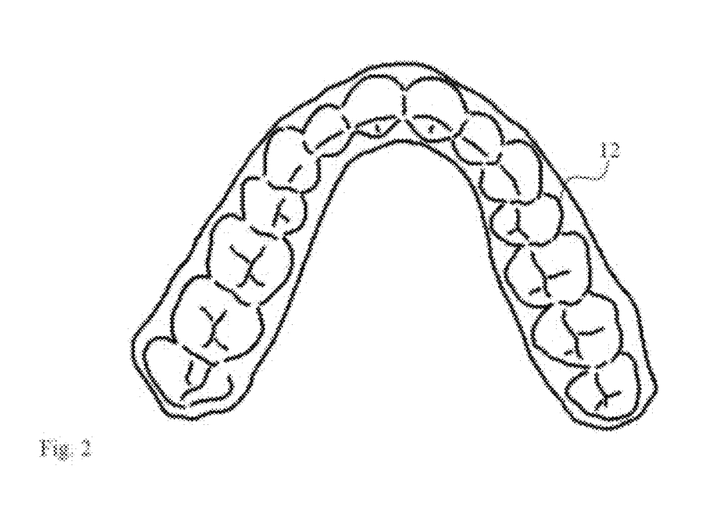

As depicted in FIG. 1, an aligner 10 extends in such a way as to follow the successive teeth D of the dental arch to which it is fitted. It defines a tray in the overall shape of a "U".

The interior surface of the aligner is referred to as the "tray" 12. The shape of the tray is determined to fix the aligner on the teeth, but also according to a target positioning desired for the teeth. More specifically, the shape is determined in such a way that, when the aligner is in its service position, it applies forces that tend to move the treated teeth toward their target positioning.

A "tooth outline" is understood to mean a line displaying the shape of a free end 22 of a tooth on an image.

Figure 4:
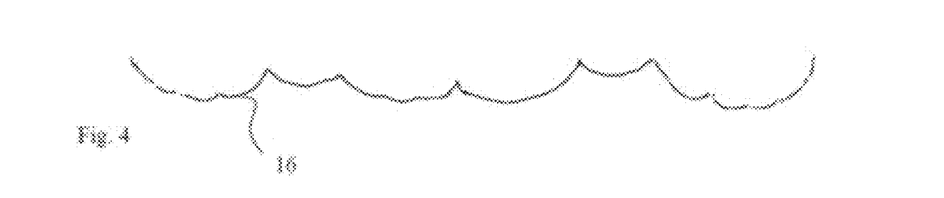
FIG. 4 depicts the dentition outline defined from the image of FIG. 3.

Of course, such a line may delimit the free end of this tooth. The tooth outline is then qualified as an "interior tooth outline" 14. A "dentition outline" 16 is made up of the set of interior tooth outlines of a set of teeth (FIG. 4).

Such a line may also delimit part of the aligner. The tooth outline is then qualified as an "exterior tooth outline" 18. In particular, the bottom 20 of the tray has a shape that substantially compliments that of the free ends 22 of the teeth. As a result, in an image depicting the bottom of the tray, the tray-bottom outline defines a set of exterior tooth outlines 18.

Figure 5:
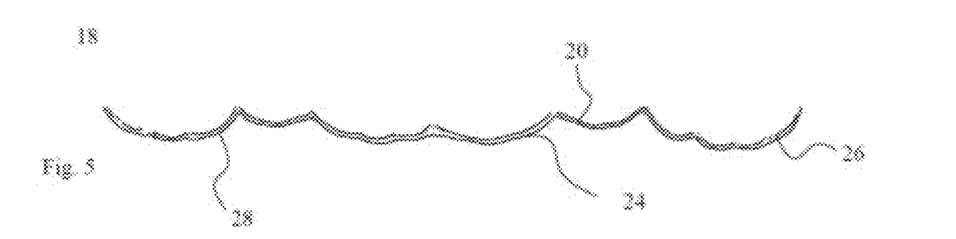
FIG. 5 depicts the aligner outlines defined from the image of FIG. 3 and capable of being used according to the invention.
Figure 6:
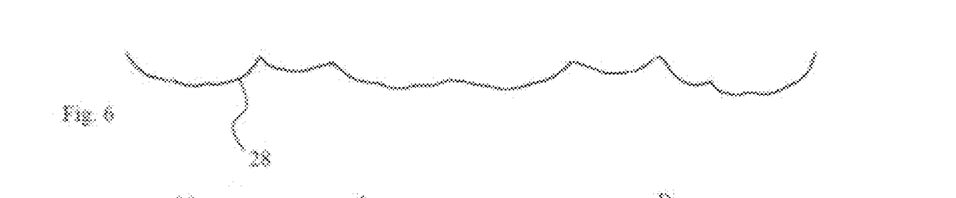
FIG. 6 depicts the aligner outline defined from the image of FIG. 3 and used in FIGS. 7 and 8 for comparing against a dentition outline.

The aligner material that separates the exterior surface 24 of the aligner and the tray 12 defines the thickness of the orthodontic aligner. This thickness may be seen in FIG. 5. Conventionally, the aligner has a substantially constant thickness. The exterior surface 24 of the aligner, which extends facing the bottom 20 of the tray, is therefore also substantially the same shape as the bottom of the tray. As a result, in an image, the outline of the exterior surface 24 of the aligner also defines a set of exterior tooth outlines 18.

An "aligner outline" 28 is made up of a set of exterior tooth outlines 18. It may therefore be defined by the bottom 20 of the tray or by the exterior surface 24 of the aligner.

When a tooth is positioned in the tray in such a way that its free end 22 is in contact with the bottom of the tray, its interior tooth outline substantially coincides with the corresponding exterior tooth outline if the exterior tooth outline 18 is defined by the bottom 20 of the tray, or is offset and substantially parallel to the corresponding exterior tooth outline if the exterior tooth outline is defined by the exterior surface 24 of the aligner.

For preference, the exterior tooth outlines used to define the aligner outline 28 are defined by the exterior surface 24 of the aligner, which is more visible.

Figure 9:
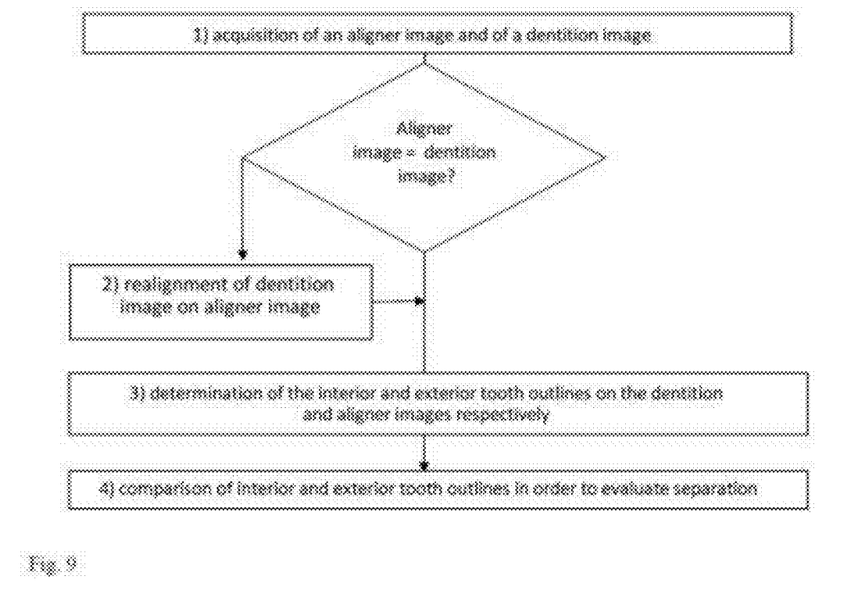
FIG. 9 schematically depicts a method according to the invention.

The method of the invention is aimed at detecting situations in which the free end 22 of a tooth is no longer in contact with the bottom of the tray, and at measuring the amplitude of this separation (FIG. 9).

In step 1), at least one image of the teeth, referred to as "updated image" is taken, using an image acquisition apparatus.

For preference, at least one reminder informing the patient of the need to create an updated image is sent to the patient. This reminder may come on paper, or, for preference, comes in electronic form, for example in the form of an email, of an automatic alert on a specialist mobile application, or of an SMS. Such a reminder may be sent by the patient's orthodontist practice or laboratory or by his dentist or by his specialist mobile application, for example.

Step 1) is performed at the instant that the evaluation of the shape of an aligner is desired, for example over 4 weeks after the start of the treatment using the aligner.

The image acquisition apparatus is preferably a mobile phone, a "connected" camera, a smartwatch, a tablet or a desktop or laptop personal computer, including an image acquisition system, such as a webcam or a camera.

The acquisition is preferably performed by the patient or someone close to the patient, but may be performed by any other individual, notably a dentist or orthodontist, preferably without imposing a requirement for the image acquisition apparatus to be positioned accurately with respect to the teeth.

For preference, the updated image is a photograph or an image extracted from a film. It is preferably in color, preferably true color.

According to the invention, the shape of the aligner is evaluated by comparing an outline of this aligner, in its service position, with an outline of the teeth wearing it.

In step 1), it is therefore necessary to acquire enough updated images to be able to make this comparison, namely at least one image of the aligner in its service position, or "aligner image", and at least one image of teeth bearing this aligner in the service position, or "dentition image".

Figure 3:
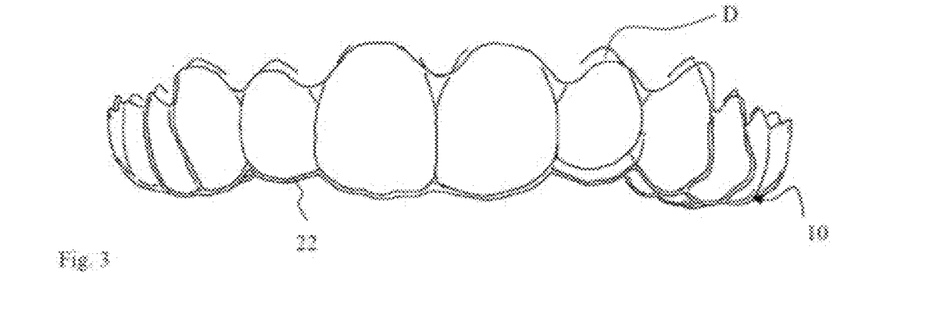
FIG. 3 depicts an updated image of a dental arch bearing an orthodontic aligner like that of FIGS. 1 and 2.

In one embodiment, the dentition image is the aligner image. In other words, the same updated image makes it possible not only to see the aligner outline 28 but also to see the dentition outline 16, through the aligner (FIG. 3). This single image therefore makes it possible to compare aligner and dentition outlines. Advantageously, readjustment step 2), described later, is not needed.

In another embodiment, the dentition image is an image of the teeth in the absence of the orthodontic aligner, referred to as the "bare dentition image". This embodiment is needed if the dentition outline 16 is not clearly visible, through the aligner, on the aligner image. The operator then takes a first image of the aligner in the service position and, at another moment, having removed the aligner, takes a second image of teeth that wear the part of the aligner depicted in the first image, namely the bare dentition image.

Because the updated images are preferably taken without any special precautions, the bare dentition image is not normally acquired under the same acquisition conditions as the aligner image. In particular, the positions in space of the acquisition apparatus with respect to the teeth and/or the adjustment thereof ("the calibration" of the acquisition apparatus), for example the amount of zoom, may differ when acquiring these two images. The aligner and dentition outlines defined from the bare dentition and aligner images respectively, are therefore not normally immediately comparable. Step 2) is intended to make these outlines comparable by redefining the dentition image.

Figure 10:
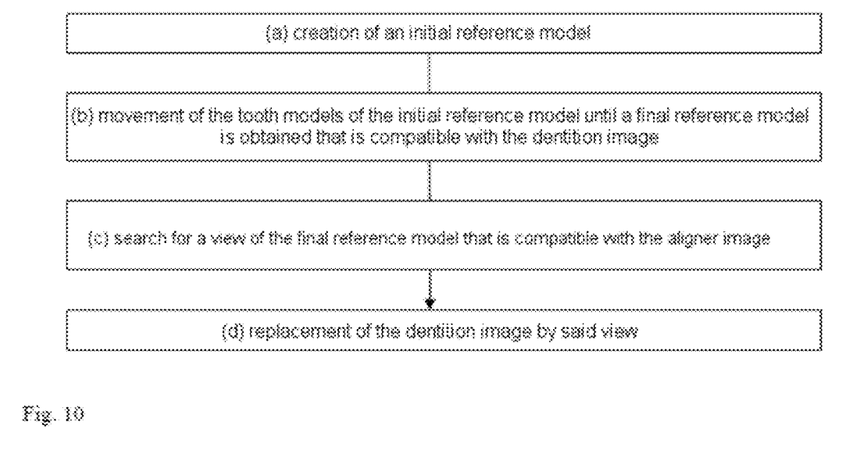

In a particularly preferred embodiment, step 2) (FIG. 10) comprises the steps (a) to (d):

Step (a) is prior to step 1).

It is preferably performed at the start of the orthodontic treatment or before the start of the treatment. It may also be performed at the start of the treatment or before the start of the treatment using the aligner.

Step (a) consists in creating a digital three-dimensional model of a dental arch bearing the teeth treated, or "initial reference model".

The initial reference model is, for example, of the .stl or .Obj, .DXF 3D, IGES, STEP, VDA, or scattergram type. Advantageously, such a model, referred to as a "3-D" model, can be viewed from any angle.

The initial reference model can be prepared from measurements taken from the teeth of the patient or from a physical model of his teeth, for example a plaster cast.

The initial reference model is preferably created by means of a professional device, for example by means of a 3-D scanner, preferably operated by a healthcare professional, for example by an orthodontist, or an orthodontistry laboratory. In an orthodontist practice, the patient or the physical model of his teeth may advantageously be arranged in a precise position and the professional apparatus may be perfected. This results in a highly accurate initial reference model. The initial reference model preferably provides information regarding the positioning of the teeth with an error of less than $5/10$ mm, preferably less than $3/10$ mm, preferably less than $1/10$ mm.

In the initial reference model, a part which corresponds to a tooth is referred to as a "tooth model". The tooth models may be defined as described, for example, in international application PCT/EP2015/074896.

Step (b) comprises modifying the initial reference model, by moving the tooth models, until a positioning of the tooth models that is compatible with the dentition image is obtained. For preference, step (b) is performed fewer than 4 weeks, fewer than 2 weeks, less than one week, preferably more or less immediately after the acquisition of the dentition image.

It preferably consists in an iterative process in which, upon each iteration, one or more tooth models are moved, then optimum conditions for acquiring the initial model thus modified (referred to as the "reference model to be tested") are determined, the optimum conditions being defined as the conditions allowing the reference model to be tested to be observed in such a way that the view of said model is as close as possible to the dentition image. Steps c) to e) described in PCT/EP2015/074896 are preferably implemented:

c) analysis of the dentition image (updated image in PCT/EP2015/074896) and creation of an updated map relating to discriminating information;

d) optionally, determination, for the dentition image, of rough virtual acquisition conditions approximating the actual acquisition conditions of said dentition image;

e) the search, using the updated map, for a final reference model corresponding to the positioning of the teeth at the time of the acquisition of the dentition image, the search preferably being carried out by means of a metaheuristic, preferably evolutionary method, preferably by simulated annealing.

All the features of steps c) to e) described in PCT/EP2015/074896 are applicable. According to step c), the dentition image is analyzed so as to create an updated map relating to at least one item of discriminating information.

"Discriminating information" is characteristic information that can be extracted from an image ("image feature"), conventionally through the computer processing of this image.

Discriminating information may exhibit a variable number of values. For example, outline information may be equal to 1 or 0 according to whether or not a pixel belongs to an outline. Brightness information may adopt a great many values. Image processing makes it possible to extract and quantify the discriminating information.

The updated map represents discriminating information in the frame of reference of the dentition image. The discriminating information is preferably chosen from the group consisting of outline information, color information, density information, distance information, brightness information, saturation information, information regarding reflections and combinations of this information.

In optional step d), the actual acquisition conditions for the dentition image acquired in step 1), namely the position and orientation in space of the acquisition apparatus with respect to the teeth and the calibration thereof are evaluated, roughly. Step d) advantageously makes it possible to limit the number of tests on virtual acquisition conditions during step e) and therefore allows step e) to be speeded up considerably.

Use is preferably made of one or more heuristic rules. For example, for preference, conditions that correspond to a position of the image acquisition apparatus behind the teeth or at a distance greater than 1 m away from the teeth, are excluded from the virtual acquisition conditions that can be tested for in step e). In a preferred embodiment, use is made of markers marked on the dentition image in order to determine a substantially conical region of the space that delimits the virtual acquisition conditions that can be tested for in step e), or "test cone".

The objective of step e) is to modify the initial reference model until a final reference model is obtained that corresponds to the dentition image. Ideally, the final reference model is therefore a digital three-dimensional reference model from which the dentition image could have been taken had this model been real.

A succession of reference models "to be tested" is therefore tested, the choice of a reference model to be tested being dependent preferably on the level of correspondence between the previously tested reference models "to be tested" and the dentition image. This choice is preferably made by following a known optimization method, particularly chosen from metaheuristic optimization methods, preferably evolutionary methods, particularly from simulated annealing methods.

For preference, step e) comprises the following steps:

e1) definition of a reference model to be tested as being the initial reference model, then e2) following the subsequent steps, testing virtual acquisition conditions with the reference model to be tested in order to achieve a fine approximation of said actual acquisition conditions;

e21) determining virtual acquisition conditions to be tested;

e22) creation of a two-dimensional reference image of the reference model to be tested under said virtual acquisition conditions to be tested;

e23) processing of the reference image to create at least a reference map at least partially representing said discriminating information;

e24) comparison of the updated and reference maps so as to determine a value for a first evaluation function, said value for the first evaluation function being dependent on the differences between said updated and reference maps and corresponding to a decision as to whether to continue or stop the search for virtual acquisition conditions approximating said actual dentition-image acquisition conditions with greater precision than said virtual acquisition conditions to be tested as determined the last time step e21) was run;

e25) if said value for the first evaluation function corresponds to a decision to continue said search, modification of the virtual acquisition conditions to be tested, then resumption from step e22);

e3) determination of a value for a second evaluation function, said value for the second evaluation function being dependent on the differences between the dentition and reference maps under the virtual acquisition conditions best approximating said actual acquisition conditions and resulting from the last running of step e2), said value for the second evaluation function corresponding to a decision to continue or stop the search for a reference model approximating the positioning of the teeth at the time of the acquisition of the dentition image with greater precision than said reference model to be tested that was used the last time step e2) was run, and if said value for the second evaluation function corresponds to a decision to continue said search, modification of the reference model to be tested by moving one or more tooth models, followed by resumption from step e2).

Steps e1) to e3) are described in detail in PCT/EP2015/074896, or WO2016066651.

The final reference model obtained at the end of step e) is a three-dimensional model resulting from successive modifications to the very precise initial reference model. Advantageously, it is thus itself very precise, even though it has been obtained from simple photographs taken without any special precautions.

Step (c), is a search for a view of the final reference model that corresponds to the aligner image. Specifically, the aligner image has been acquired under actual acquisition conditions in which the teeth were insufficiently visible. The purpose of step (c) is to determine a view of the final reference model that is compatible with the aligner image, namely a view representing the teeth as they would have been represented on the aligner image had they been sufficiently visible.

In particular, this search leads to a virtual movement of a virtual image acquisition apparatus around the final reference model until a "readjusted" position compatible with the aligner image is found, namely a position in which teeth or parts of teeth can be observed as they would have been represented on the aligner image had the aligner been transparent.

For preference, the search for the view of the final reference model that best corresponds to the aligner image is performed by iteration, preferably by means of a heuristic method, more preferably still by means of one of the methods described hereinafter. These methods advantageously make it possible to guide the virtual movement of the virtual image acquisition apparatus around the final reference model in order to speed up the determination of said readjusted position.

In order to readjust the virtual image acquisition apparatus, it is necessary to identify, in the aligner image, markings of which the position in the final reference model is known. Such markings may generally be identified. Failing that, it is necessary to acquire a new aligner image and to repeat the search for such markings.

The markings preferably belong to teeth that are known to be immobile, for example because they are not being treated (if such teeth are visible on the aligner image) or to parts of the aligner in contact with such teeth, which are therefore likewise immobile. The immobile teeth can be easily identified during step (c), because these are teeth the tooth model of which has not been moved during step (b).

The readjustment entails the use of at least three non-aligned points as markers.

The final reference model is then observed under various virtual acquisition conditions until a view of the final reference model is obtained that is compatible with the aligner image, which means to say in which the markers have identical relative positions. The virtual image acquisition apparatus is then in the readjusted position.

In step (d), the dentition image is replaced with the final view of the reference model observed in the readjusted position, namely under the virtual acquisition conditions determined in step (c).

Indeed the final reference model represents, in three dimensions, the teeth in their positioning at the instant at which the dentition image was acquired, in step 1). Moreover, the virtual acquisition conditions determined in step (c) are substantially identical to the actual acquisition conditions at the instant at which the aligner image was taken in step 1). By observing the final reference model under the virtual acquisition conditions determined in step (c), the teeth are therefore observed at the moment at which the dentition image was taken, under the image acquisition conditions of the aligner image. The view of the final reference model under these virtual acquisition conditions is therefore comparable with the aligner image and therefore replaces the dentition image acquired in step 1). For the sake of clarity, this view is also referred to as "dentition image", which means to say that the view is converted into the dentition image.

The shapes and dimensions of the outlines on the dentition image thus defined are therefore comparable with those of the outlines on the aligner image.

Step 3), determines, for each of a plurality of teeth represented in the dentition and aligner images, the interior and exterior tooth outlines.

A person skilled in the art knows how to process an image in order to isolate an outline. This processing for example involves the well-known application of masks or filters, which come with image processing software. Such processing operations for example make it possible to detect the regions of greatest contrast.

These processing operations notably comprise one or more of the following known and preferred methods, namely:

by application of a Canny filter, notably to search for outlines using the Canny algorithm;

by application of a Sobel filter, notably for calculating derivatives by means of the extended Sobel operator;

by application of a Laplace filter to calculate the Laplacian of an image;

by detecting blobs on an image ("Blobdetecor");

by applying a "Threshold" to apply a fixed threshold to each element of a vector;

by resizing, using relationships between pixel zones ("Resize(Area)") or bi-cubic interpolations on the pixel environment;

by image erosion by means of a specific structuring element;

by image expansion by means of a specific structuring element;

by image correction, particularly using regions in the vicinity of the restored zone;

by application of a bilateral filter;

by application of Gaussian blurring;

by application of an Otsu filter, to look for the threshold that minimizes variance between classes;

by application of an A*filter, to search for a path between points;

by application of an "Adaptive Threshold" for applying an adaptive threshold to a vector;

by application of a histogram equalization filter to an image in grayscale in particular;

by "BlurDetection", to calculate the entropy of an image using its laplacian;

by detecting outlines ("FindContour") of a binary image;

by filling with color ("FloodFill"), notably to fill a connected element with a determined color.

The following nonlimiting methods, although not preferred, can also be used:

by application of a "MeanShift" filter so as to find an object on a projection of the image;

by application of a "CLAHE" filter, which stands for "Contrast Limited Adaptive Histogram Equalization";

by application of a "Kmeans" filter, to determine the center of clusters and of groups of samples around clusters;

by application of a DFT filter, so as to perform a direct or inverse Discrete Fourier Transform on a vector;

by calculating moments;

by application of a "HuMoments" filter to calculate invariant Hu invariants;

by calculating the integral of an image;

by application of a Scharr filter, making it possible to calculate a derivative of the image by using a Scharr operator;

by searching for the convex envelope of points ("ConvexHull");

by searching for the set of convex points of an outline ("ConvexityDefects");

by shape comparison ("MatchShapes");

by checking whether points form a part of an outline ("PointPolygonTest"); by Harris outline detection ("CornerHarris");

by looking for minimum eigenvalues in matrices of gradients, in order to detect the corners ("CornerMinEigenVal");

by application of a Hough transform in order to find circles in a grayscale image ("HoughCircles");

by "Active contour modeling" (plotting the outline of an object from a potentially "noisy" 2-D image);

by calculating a field of forces, termed GVF ("gradient vector flow"), in part of the image;

by "CascadeClassification".

Tooth outline determination can be optimized by following the teachings of PCT/EP2015/074900.

In step 4) of comparing the outlines, the procedure is preferably in accordance with one of the two particular embodiments hereinbelow, corresponding respectively to FIGS. 7 and 8: In a first particular embodiment, step 4) comprises steps i) to iii) for each of a plurality of teeth for which interior and exterior tooth outlines have been determined.

Figure 7:
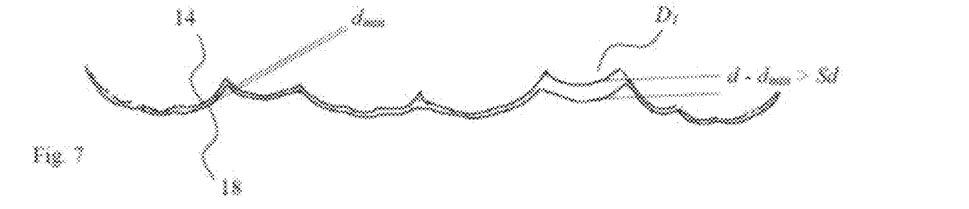
FIGS. 7 and 8 depict the dentition and aligner outlines of FIGS. 4 and 6 as depicted on the updated image of FIG. 3.

In step i), a distance d between the interior and exterior tooth outlines of each of said teeth is determined (FIG. 7).

The distance between the interior 14 and exterior 18 tooth outlines of a tooth may for example be the mean distance or the maximum distance between the pixels of said outlines corresponding to one and the same point on the tooth.

The distance is preferably measured in pixels, which advantageously avoids the need to establish the scale of the dentition and aligner images.

In step ii), a distance threshold Sd is determined, preferably using the distances determined in step i).

For preference, in step ii), the distance threshold Sd is substantially equal to the smallest of the distances determined in step i) ($d_{min}$). Conventionally, in step 1), at least one of the teeth being treated is in contact with the bottom of the tray in which it is inserted. The distance between the interior and exterior tooth outlines of this tooth is then equal to a minimum distance $d_{min}$ corresponding to a normal situation. It can therefore be used as a benchmark in order, in step iii), to evaluate the distances between the interior and exterior teeth outlines of the other teeth.

In step iii), a score known as the "distance score" S(d,Sd), is determined, for each of the teeth, as a function of the distance d between the interior and exterior tooth outlines and of the distance threshold Sd.

For preference, the distance score for a tooth is equal to S(d,Sd) namely the difference between the distance between the interior and exterior tooth outlines for this tooth and the distance threshold. The higher the distance score, the greater the separation of the tooth concerned from the tray.

FIG. 7 illustrates one example of implementation of steps i) to iii), in which a tooth D1 has separated from the bottom of the tray and such that $d-d_{min}>Sd$.

In a second particular embodiment, step 4) comprises the steps i') to iii').

Step i') considers at least one triplet made up of first, second and third teeth, D1, D2 and D3 respectively, the first and third teeth being adjacent to the second tooth, which means to say that the first, second and third teeth succeed one another along a dental arch.

The dentition and aligner outlines comprising the respective interior tooth outlines $14_1$, $14_2$ and $14_3$, and respective exterior tooth outlines $18_1$, $18_2$ and $18_3$, of respective teeth D1, D2 and D3, are determined.

An interior or exterior "offset" respectively, represents a distance between the, respectively interior or exterior, tooth outlines of two adjacent teeth.

The following are determined an offset between the interior tooth outline of said first tooth $14_1$ and the interior tooth outline of said second tooth $14_2$, and referred to as the "first interior offset", $\Delta_{1-2}i$;

an offset between the interior tooth outline of said second tooth $14_2$ and the interior tooth outline of said third tooth $14_3$, and referred to as the "second interior offset", $\Delta_{2-3}i$;

an offset between the exterior tooth outline of said first tooth $18_1$ and the exterior tooth outline of said second tooth $18_2$, and referred to as the "first exterior offset", $\Delta_{1-2}e$;

an offset between the exterior tooth outline of said second tooth $18_2$ and the exterior tooth outline of said third tooth $18_3$, and referred to as the "second exterior offset", $\Delta_{2-3}e$;

The interior offset between the interior tooth outlines of two adjacent teeth is preferably equal to the largest distance between the interior tooth outlines of these two teeth on the dentition outline.

The exterior offset between the exterior tooth outlines of two adjacent teeth is preferably equal to the largest distance between the exterior tooth outlines of these two teeth on the aligner outline.

The interior offsets and the exterior offsets are preferably measured in pixels, which advantageously avoids the need to establish the scale of the dentition and aligner images.

Figure 8:
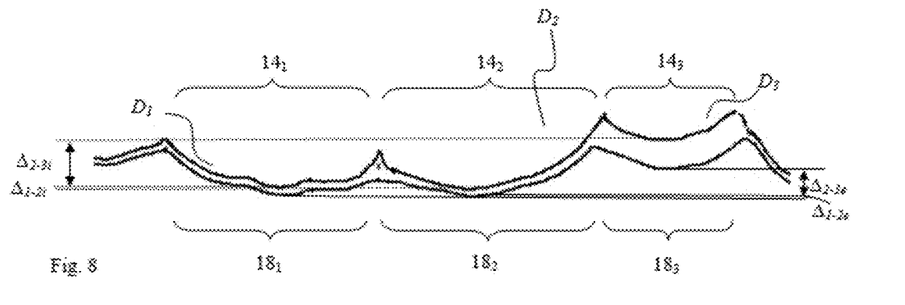

The following are then determined:
 the difference between the first interior offset $\Delta_{1-2}i$ and the first exterior offset $\Delta_{1-2}e$, referred to as "first offset difference" $\Delta_{1-2}$ $(=\Delta_{1-2}i-\Delta_{1-2}e)$;
 the difference between the second interior offset $\Delta_{2-3}i$ and the second exterior offset $\Delta_{2-3}e$, referred to as "second offset difference" $\Delta_{2-3}$ $(=\Delta_{2-3}i-\Delta_{2-3}e)$;

In the example of FIG. 8, $\Delta_{1-2}$ is far smaller than 42-3.

Step ii'), determines an offset-difference threshold SA, preferably from the first and second offset differences $\Delta_{1-2}$ and $\Delta_{2-3}$ determined in step i').

For preference, in step ii'), the offset threshold is substantially equal to the smallest of the offset differences determined in step i').

Conventionally, in step 1), at least two adjacent teeth being treated are in contact with the bottom of the tray in which they are inserted. The difference in offset between these two treated teeth is then substantially zero. This zero difference in offset corresponds to a normal situation and can therefore be used as a benchmark for evaluating the differences in offset between adjacent treated teeth.

In FIG. 8, the difference in offset between two teeth $D_1$ and $D_2$ is substantially zero.

In step iii'), at least one score known as the "offset score", is determined, for each pair of teeth of said triplet, as a function of the difference in offset with a tooth adjacent to said tooth and of the offset-difference threshold.

In particular, the difference in offset of the first tooth with the second tooth may be compared against the offset-difference threshold SA, for example of zero. The offset-difference threshold may notably be subtracted from the offset difference of the first tooth with respect to the second tooth in order to determine a score for the offset between the first and second teeth.

This offset score indicates, for example if it is positive, that one or each of the first and second teeth is liable to be separated from the bottom of the tray.

In FIG. 8, the difference in offset between the two teeth $D_2$ and $D_3$ is positive, which is an indication that the second or third tooth has separated.

In FIG. 8, since the difference in offset between the two teeth $D_1$ and $D_2$ is substantially zero, the positive difference in offset between the two teeth $D_2$ and $D_3$ therefore indicates that the third tooth has separated.

In general, when a first offset score for first and second teeth indicates the separation of one of these two teeth, a second offset score is determined for the second tooth and a third tooth adjacent to the second tooth. If the second offset score is lower than the first offset score, it is probable that it is the first tooth that has separated from the bottom of the tray. If not, it is probably the second tooth that has separated.

In step 5), information, for example an alert, is sent to an operator to inform him, if appropriate, that the situation is abnormal. The information relating to a tooth is dependent on the score or scores established in step 4). For preference, the information comprises a value making it possible to quantify, for at least one tooth, the level of separation of the aligner over this tooth, this value preferably being established from the score or scores calculated for this tooth in step 4).

In one embodiment, this information is used to establish a diagnosis and/or to modify the treatment, particularly to recommend a change in aligner and/or to determine the characteristics of a future aligner for the patient.

Generalization to the Previous Invention ("Generalized Invention") The invention described hereabove may be generalized to evaluate an orthodontic appliance worn by a patient.

The generalized invention relates to a method for evaluating an orthodontic appliance worn by a patient, said method comprising the following steps:
 1') at an "appliance" instant, acquisition of at least one two-dimensional image of teeth of said patient, said image, referred to as "appliance image", at least partially representing the orthodontic appliance in a service position in which it is worn by said teeth;
  at a "dentition" instant, acquisition of at least one two-dimensional image of said teeth of said patient, referred to as "dentition image", said dentition image therefore also representing said orthodontic appliance if said orthodontic appliance is being fixed on said teeth or born by said teeth;
 2') if a determination of dental and appliance attributes to be compared at following step 4') and relative to the shape of a tooth represented on the at least one dentition image and relative to the shape of the orthodontic appliance on the at least one appliance image, respectively, is not possible, from said at least one appliance image and from said at least one dentition image, respectively, conversion of the at least one appliance image and/or of the at least one dentition image so that said at least one appliance image be compatible with said at least one dentition image;
 for each of a plurality of teeth represented on the dentition and appliance images:
 3') determination of dental and appliance attributes relative to the shape of the tooth represented on the dentition image and relative to the shape of the orthodontic appliance on the appliance image respectively,
 4') comparison of the dental and appliance attributes, followed by determination of at least one score according to said comparison;
 5') optionally, comparison of the score against an acceptability threshold and emission of information according to the result of the comparison.

In an embodiment, at step 2'), if said at least one appliance image is not compatible with said at least one dentition image, the at least one appliance image and/or of the at least one dentition image is converted so that said at least one appliance image be compatible with said at least one dentition image, The determination of the dental and appliance attributes at step 3') may comprise:
 the determination of an outline of the tooth and of the orthodontic appliance on the dentition and appliance images respectively, or the determination of a surface of the tooth and of the orthodontic appliance represented on a plurality of dentition images and on a plurality of appliance images, respectively.

The aligner image is a specific appliance image, in which the orthodontic appliance is an aligner.

The interior and exterior tooth outlines representing the outline of the free end of a tooth on the dentition and aligner images, respectively, are specific dental and appliance attributes relative to the shape of the tooth represented on the dentition image considered at step 3') and relative to the shape of the orthodontic appliance on the appliance image respectively.

The "updated images" are specific examples of appliance and dentition images which are acquired substantially simultaneously, i.e. refer to a specific situation in which the appliance and dentition instants are substantially simultaneous and correspond to an "actual instant" at which step 1) is achieved.

The generalized invention preferably also has one or more of the following optional features:
- the orthodontic appliance is chosen among
  - an aligner,
  - a part which is rigidly fixed on a tooth, in particular glued on a tooth, preferably chosen among
    - an attachment fixed on a tooth to be interposed between said tooth and an aligner in the service position,
    - a button fixed on a tooth for an attachment of an elastic band,
    - a bracket fixed on a tooth for an attachment of a metallic wire,
    - a spring,
    - a temporary anchorage device, or "TAD",
  - a palatal expander appliance;
- at least one of said at least one appliance image and/or at least one of said at least one dentition image is acquired with a mobile phone;
- at least one of said at least one appliance image and/or at least one of said at least one dentition image is acquired by the patient or one of him or her close relatives;
- the appliance and dentition instants are simultaneous, the appliance and dentition images being possibly generically referred to as "updated image";
- the appliance and dentition images are extraoral images;
- the appliance and dentition images are photographs or extracted from a film, possibly taken without special precaution, for example by the patient. The number of orthodontist appointments can therefore be limited;
- the dental and appliance attributes may be an outline of the tooth and of the orthodontic appliance on the dentition and appliance images respectively, or a surface of the tooth and of the orthodontic appliance on the dentition and appliance images, respectively;
- step 4') comprises the following steps:
  - i) for each of a plurality of teeth for which the dental and appliance attributes have been determined, determination of a difference, or "distance", between the dental and appliance attributes;
  - ii) determination of a distance threshold, preferably using the distances determined in step i);
  - iii) for each of said teeth, determination of a distance score dependent on
    - the distance between the dental and appliance attributes, and
    - the distance threshold;
- said distances are measured in pixels;

in step ii), the distance threshold is dependent on the smallest of the distances determined in step i),
- at step 5'), the information indicates
  - whether said orthodontic appliance, intended to be fixed on a tooth, has come off said tooth and is still present in the mouth, and/or
  - whether said orthodontic appliance, intended to be fixed on a tooth, has come off said tooth and is not present in the mouth anymore, and/or
  - whether said orthodontic appliance has changed of shape between the dental instant and the appliance instant, and/or
  - whether said orthodontic appliance correctly matches a surface of a tooth;
- at step 5'), the information is sent to a mobile phone of the patient and/or to a dental care professional, in particular an orthodontist.

Optional features of steps 1) to 5) may possibly be applied to steps 1') to 5'), respectively, when they are technically compatible.

In an embodiment, said dentition and appliance images are one and the same image.

In an embodiment, the dentition and appliance images are not compatible, and the method comprises the following steps:
- (a') prior to step 1'), for preference at the start of the orthodontic treatment or before the start of the orthodontic treatment, creation of a digital three-dimensional model of at least part of a dental arch bearing said teeth, or "initial reference model" and, for each tooth of the initial reference model, definition of a digital three-dimensional reference model of said tooth, or "tooth model";
- (b') modification of the initial reference model by moving the tooth models until a final reference model compatible with the dentition image or with the appliance image is obtained;
- (c') search for a two-dimensional view of the final reference model that is compatible with the appliance image or the dentition image, respectively;
- (d') conversion of the dentition image or of the appliance image, respectively, into said view;

Optional features of steps (a) to (d) may possibly be applied to steps (a') to (d'), respectively.

Example: Evaluating an Orthodontic Appliance from Updated Images, i.e. from Dental and Appliance Images Acquired Substantially Simultaneously In particular, the generalized invention allows for a check whether an orthodontic appliance such as a bracket for the attachment of an arch, usually a metallic wire, has come off a tooth.

To check whether a bracket has come off a tooth, it is preferred that the appliance attribute is an outline (or "contour") of said bracket, and that the dental attribute is an outline of the tooth on which said bracket is intended to be fixed. The score may measure the position of the appliance attribute relative to the dental attribute. In particular, the score may be the distance between the appliance attribute and the dental attribute. The acceptability threshold may be a range for said score. The acceptability threshold may be parametrized by a dental care professional, in particular an orthodontist, preferably according to the patient's teeth configuration and/or the orthodontic treatment.

For instance, the dental care professional, in particular the orthodontist, may fix the bracket on the tooth so that the left part of the bracket complete outline (appliance attribute) be at a distance of about 1 mm from the left part of the tooth complete outline (dental attribute), at the frontier with an adjacent tooth on the left of the tooth on which the bracket is fixed. The dental care professional, in particular the orthodontist, may parameterize the acceptability threshold to be the range ">0.5 mm and <1.5 mm", so that an information be emitted if the distance between the left part of the bracket complete outline and the left part of the tooth complete outline (score) is less than 0.5 mm or greater than 1.5 mm.

The dentition image will preferably be the same as the appliance image, so that the appliance image represents both the left part of the bracket complete outline and the left part of the tooth complete outline. The distance between the left part of the bracket complete outline and the left part of the tooth complete outline may be measured. The acceptability threshold has been determined so that, when the bracket is correctly fixed on the tooth, this distance is between 0.5 and 1.5 mm. If the bracket comes off the tooth, it will usually move on the arch, so that the distance will not belong to this acceptability threshold anymore. A comparison of this distance with this acceptability threshold will thereby enable a detection of the bracket coming off the tooth, and the emission of a corresponding information.

As a general matter, the appliance attribute may be compared with other parts of the tooth outline, for instance to determine the mesial distance or the distal distance with an adjacent tooth, or with the occlusal edge of the tooth, or with the gingival edge of the tooth.

At step 5'), said information, for example an alert, is sent to an operator to inform him/her, if appropriate, that the situation is abnormal. The information relating to a tooth is dependent on the score established in step 4'). For preference, the information comprises a value making it possible to quantify, for at least one tooth, the level of separation of the bracket over this tooth, this value preferably being established from the score calculated for this tooth in step 4'). In particular, the value may determine if a bracket comes off the tooth.

In one embodiment, this information is used to establish a diagnosis and/or to modify the treatment, and/or to recommend an appointment.

This method to check whether a bracket has come off a tooth is well adapted with extraoral updated images, in particular acquired from the right of the patient, and/or from the left of the patient, and/or in front of the patient. However, it may not be efficient if the bracket has not moved along the arch, in particular if the updated images are acquired in front of the patient.

Figure 11:
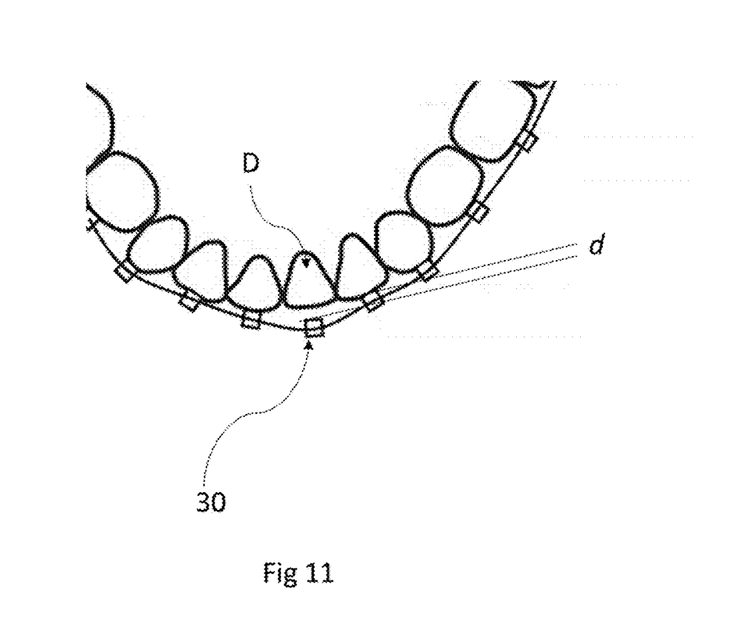

FIG. 11 illustrates another embodiment wherein the patient wears an arch and brackets appliance 30.

In this embodiment, the dentition image is the appliance image.

The dentition and appliance images may be occlusal (FIG. 11).

Similarly to the examples described above, at step 3'), the dental and appliance attributes are determined. Preferably, the dental attribute is the outline of the tooth D and the appliance attribute is the outline of the orthodontic appliance 30. At step 4'), the dental attribute and the appliance attribute are compared.

In a particular embodiment, step 4') comprises steps i) to iii) for each of a plurality of teeth for which dental and appliance attributes have been determined.

In step i), a distance d between the dental and appliance attributes of each of said teeth is determined. The distance is preferably measured in pixels.

In step ii), a distance threshold Sd is determined. In such embodiment, the distance threshold is preferably zero. Indeed, the brackets of the orthodontic appliance should be fixed on the teeth.

Alternatively, the distance threshold is equal to the smallest of the distance determined in step i). It makes it possible to take into account measurement errors.

At step iii), a score is determined for each of the teeth as a function
- of the distance d between the dental and appliance attributes and
- of the distance threshold Sd.

For preference, the score for a tooth is equal to the difference between the distance between the dental and appliance attributes for this tooth and the distance threshold.

In FIG. 11, the distance between the tooth D and the orthodontic appliance is greater than the distance threshold Sd.

At step 5'), an information, for example an alert, is sent to an operator to inform him/her, if appropriate, that the situation is abnormal, as disclosed previously.

Example: Checking a Palatal Expander Appliance

Figure 12:
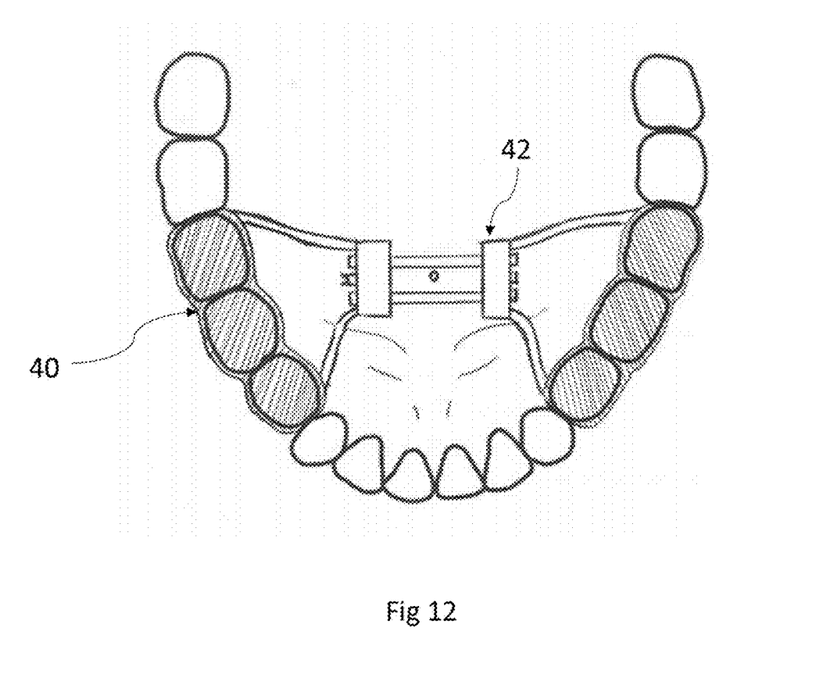

In another embodiment, the invention is applied to evaluate palatal expander appliance and in particular a bonded palatal expander appliance which preferably comprises two acrylic bite blocks 40 configured to fit teeth of the patient in a service position, the blocks being connected by an expansion structure 42 configured to fit part of the palate (FIG. 12).

In the same way as with an aligner, a method according to the invention may allow to detect the detachment of at least a part of a block.

Preferably at step 1'), a dentition image is acquired by the patient or one of him or her close relative, the dentition image being an appliance image.

At step 3'), a dental attribute and an appliance attribute are determined. The dental attribute and the appliance attribute are preferably an outline of the tooth and an outline of the appliance.

Then, at step 4'), the dental and appliance attributes are compared. The comparison at step 4) preferably comprises steps i) to iii) for each of a plurality of teeth for which dental and appliance attributes have been determined.

Example: Evaluating an Orthodontic Appliance from Dental and Appliance Images Acquired at Different Instants The methods described hereabove are based on updated images which are acquired substantially at the same instant, i.e. the actual instant. To analyse the dental situation for a tooth, the updated images must allow for the determination of the appliance and dental attributes, for instance represent outlines of the tooth and of the orthodontic appliance. If the orthodontic appliance is an aligner, it is easy for the patient to put the aligner in the service position to determine the appliance attribute. If the orthodontic appliance is a bracket, it normally remains visible on the updated images when it comes off the tooth. Indeed, it remains attached to the arch.

However, these methods are not adapted when the orthodontic appliance has come off the tooth and has left the mouth.

In particular, there is a need to evaluate a fixation of an attachment fixed on a tooth to be interposed between a tooth and an aligner in the service position, and/or of a button fixed on a tooth for an attachment of an elastic band. Contrary to a bracket which usually remain attached to the arch, such orthodontic appliances (i.e. attachment or button) usually leave the mouth when they come off the teeth so that they cannot be represented on the images any more.

In an embodiment of the generalized invention, the appliance and dentition images are acquired at different instants, or "appliance instant" and "dentition instant", respectively. This enables the evaluation whether an orthodontic appliance initially worn by a patient is still being worn at a posterior instant, as explained hereafter. This may also allow to evaluate a change in the shape of an orthodontic appliance worn by a tooth of a patient, and in particular a bracket, an attachment or a button. A change in the shape may in particular result from abrasion.

The appliance instant may in particular be at an instant when the orthodontic appliance is correctly fixed on the teeth of the patient and has its initial shape, and in particular at the beginning of an orthodontic treatment. It may also be at an intermediary step of the orthodontic treatment prior the dentition instant.

The dentition instant may in particular be at any time during the orthodontic treatment.

The time interval between the appliance instant and the dentition instant may in particular be greater than 4 days, 1 week, 2 weeks or 4 weeks, and/or less that 6 months, 4 months or two months.

The appliance instant may be before or after the dentition instant.

Example: Checking Whether an Orthodontic Appliance Initially Worn by a Patient has been Removed In particular, the generalized invention allows for a check whether an orthodontic appliance, in particular a bracket, an attachment or a button, has come off a tooth, or for a check of a change of shape of the orthodontic appliance, in particular a bracket, an attachment or a button.

For this check, it is preferred that the appliance attribute and the dental attribute be a surface of the tooth model, while considering that the orthodontic appliance belongs to the tooth model. The determination of a surface requires several images and may be achieved according to the basic principles of 3D modelling with a scanner.

This surface is named "appliance surface" and "dental surface" when determined from appliance images and from dentition images, respectively.

For an orthodontic appliance which is normally fixed on the extrados of a tooth, at the appliance instant, this surface i.e. the appliance surface, would be the extrados surface of the assembly of the orthodontic appliance and of the tooth.

If the orthodontic appliance has come off the tooth, it is not represented on the dentition images, so that said surface at the dentition instant, i.e. the dental surface, is the extrados surface of the tooth.

The above example relates to an orthodontic appliance which is fixed on the extrados of a tooth, but it may be applied to attachments or brackets bonded on the intrados of the tooth. In this embodiment, using occlusal pictures to complement or instead of extra-oral images is preferred.

The appliance instant is preferably before the dentition instant.

The appliance instant is preferably at the beginning of an orthodontic treatment, when the orthodontic appliance which is normally fixed on the considered tooth.

The dentition instant is preferably during the orthodontic treatment. The dentition images are preferably acquired with a mobile phone by the patient or one of him or her close relatives.

If the orthodontic appliance has not come off the tooth and has kept its shape since the appliance instant, it is represented on the dentition images, so that the dental surface is the extrados surface of the assembly of the tooth and of the orthodontic appliance. The dental surface is therefore the same as the appliance surface.

If the orthodontic appliance has not come off the tooth and has changed its shape since the appliance instant, for instance because it has been broken or abraded, it is represented on the dentition images, so that the dental surface is also the extrados surface of the assembly of the tooth and of the orthodontic appliance. But the dental surface is not the same as the appliance surface.

The score may measure the difference between the area of the appliance surface and the area of the dental surface.

The acceptability threshold may be a range for the score. The acceptability threshold may be parametrized by a dental care professional, in particular an orthodontist.

For instance, the dental care professional, in particular the orthodontist, may have determined that the area of the orthodontic appliance in contact with the tooth is 2 mm$^2$, and parameterize the acceptability threshold to be "2 mm$^2$", so that an information be emitted if the difference of areas between the dental surface and the appliance surface is not 2 mm$^2$.

Alternatively, the score may be the average distance between the appliance surface and the dental surface.

For instance, the dental care professional, in particular the orthodontist, may parameterize the acceptability threshold to be "=0 mm", or to be the range "<0.05 mm" to take into account measurement errors, or to be the range "<0.2 mm" to take into account an acceptable deformation of the orthodontic appliance, so that an information be emitted if the distance is not 0, or is 0.05 mm or more, or is 0.2 mm or more, respectively.

If the orthodontic appliance comes off the tooth between the appliance instant and the dentition instant, the surface of the assembly of the tooth and of the orthodontic appliance, represented by the appliance surface on the appliance images, will become the surface of the sole tooth, represented by the dental surface on the dentition images. The average distance between the appliance surface and the dental surface will not be null. A comparison of this distance with the acceptability threshold will thereby enable a detection of this coming off the tooth, and the emission of a corresponding information.

For the conversion of the appliance image at step 2'), the method preferably comprises the following steps:
(a') prior to the acquisition of the appliance image, for preference at the beginning of the orthodontic treatment or before the beginning of the orthodontic treatment, creation of a digital three-dimensional model of at least part of a dental arch bearing said teeth, or "initial reference model" and, for each tooth of the initial reference model, definition of a digital three-dimensional reference model of said tooth, or "enriched tooth model", any orthodontic appliance, in particular any bracket, attachment or button, fixed, in particular glued, on a tooth being also represented in said enriched tooth model, i.e. being a part of the enriched tooth model;

(b') modification of the initial reference model by moving the enriched tooth models until a final reference model compatible with the appliance image is obtained;
(c') search for a two-dimensional view of the final reference model that is compatible with the dentition image;
(d') conversion of the appliance image into said view.

Optional features of steps (a) to (d) may possibly be applied to these steps (a') to (d'), respectively, when they are technically compatible. They may however require to be adapted to take into account that these steps (a') to (d') apply to the conversion of the appliance image, and not to the dentition image.

The conversion of the appliance image at step 2') is optional. Indeed, it is only necessary if the dentition and appliance images are not compatible, or if comparable dental and appliance attributes (at step 4')) cannot be determined from non compatible dentition and appliance images. In particular, a neural network may be trained to determine comparable dental and appliance attributes from non compatible dentition and appliance images.

Example: Determination of Dental and Appliance Attributes by Means of a Neural Network A "neural network" or "artificial neural network" is a set of algorithms well known to a person skilled in the art.

In one embodiment, at step 3'), at least one neural network is used to determine the dental and appliance attributes, the neural network being trained to determine from one or several appliance image(s) and from one or several dentition images, an appliance attribute and a dental attribute for represented teeth, respectively.

The neural network may in particular be chosen from the networks specializing in the classification of images, called "CNN" ("convolutional neural network"), for example
AlexNet (2012)
ZF Net (2013)
VGG Net (2014)
GoogleNet (2015)
Microsoft ResNet (2015)
Caffe: BAIR Reference CaffeNet, BAIR AlexNet
Torch:VGG_CNN_S,VGG_CNN_M, VGG_CNN_M_2048,VGG_CNN_M_10 24,VGG_CNN_M_128,VGG_CNN_F,VGG ILSVRC-2014 16-layer,VGG
ILSVRC-2014 19-layer,Network-in-Network (Imagenet & CIFAR-10)
Google: Inception (V3, V4).
The above list is not limiting Initially, a learning base is created comprising more than 1000, preferably more than 5000, preferably more than 10 000, preferably more than 30 000, preferably more than 50 000, preferably more than 100 000 historical images.

The learning base may be constructed according to any method, for example be created manually. To create a historical image of the learning base, an operator, preferably an orthodontist, identifies one or more "historical" tooth zones on an image, then assigns, to each identified historical tooth zone, an attribute. The "description" of the image denotes the information relating to the definition of the tooth zones of this image and to the attributes which are associated with them.

The neural network is trained with the learning base by a learning process called "deep learning". By presenting, as input for the neural network, historical images (an image and the description of the image), the neural network progressively learns to recognize patterns on an image, and to associate them with tooth zones and with an attribute for each tooth zone.

Through its training, the neural network is capable of analyzing an image and of recognizing said patterns therein. It may in particular determine a probability relating to:
the presence, at a location in said image, of a zone representing, at least partially, a tooth, or "tooth zone",
the attribute of the tooth represented on said tooth zone.

For example, the neural network is capable of determining that there is a 95% chance that a tooth zone represents an orthodontic appliance. The attribute may therefore have two values: "presence of an orthodontic appliance" and "absence of an orthodontic appliance".

When the neural network is provided, as an input, with dentition or appliance images, it will therefore be able to provide, as an output, whether these images represent or not an orthodontic appliance, for instance an attachment on the tooth. For example, if an attachment has come off between the dentition instant and the appliance instant, the dental attribute will be "absence of attachment" and the appliance attribute will be "presence of attachment".

The neural network may be trained to determine other attributes from a dentition image and an appliance image, for instance to evaluate the area of an extrados surface of a tooth represented in a tooth zone. This area is different whether the tooth is bearing an orthodontic appliance or not, for instance an attachment. If an attachment has come off between the dentition instant and the appliance instant, the dental attribute will therefore be different areas.

In an embodiment, no conversion is therefore necessary at step 2'). In particular, the neural network may be trained to determine comparable appliance and dental attributes, even if the appliance and dentition images were not acquired under the same acquisition conditions.

The same trained neural network may be used to determine both dental and appliance attributes when these attributes refer to the same parameter, for instance both relates to the presence or the absence of an orthodontic appliance on a tooth.

Different trained neural network may be used to determine the dental and appliance attributes, provided that these attributes may be compared at step 4').

The invention also relates to a method of adapting an orthodontic treatment, in which method an evaluation method according to the generalized invention is implemented and then, according to the result of said evaluation, a new orthodontic appliance is manufactured, or an appointment with a dental care professional, in particular an orthodontist, is scheduled.

The generalized invention also relates to:
a computer program and, in particular a specialist application for a mobile telephone, comprising program code instructions for executing one or more, preferably all, of steps 1') to 4'), preferably 1') to 5'), when said program is run by a computer,
a computer medium on which such a program is recorded, for example a memory or a CD-ROM; and
a personal device, in particular a mobile phone or a tablet, on which such a program is loaded.

The invention also relates to a system comprising:
a three-dimensional scanner able to implement step (a'), and
a personal device, preferably a mobile telephone, loaded with a program according to the generalized invention.

As is now clearly apparent, a method according to the invention makes it possible, from simple photos or a simple film, to determine the regions in which the aligner has come away from the teeth and evaluate the extent of this separation. It also makes it possible to determine the deformation and/or detachment of a bracket, of a block of a palatal expander, of a button fixed on a tooth for an attachment of an elastic band or of an attachment fixed on a tooth to be interposed between a tooth and an aligner in the service position.

Of course, the invention is not restricted to the embodiments described hereinabove and depicted.

Finally, the patient is not limited to a human being. In particular, a method according to the invention can be used on another animal.

The invention claimed is:

1. A method for evaluating an orthodontic appliance worn by a patient, said method comprising the following steps:
   1') at an "appliance" instant, acquisition of at least one two-dimensional image of teeth of said patient, said image, referred to as "appliance image", at least partially representing the orthodontic appliance in a service position in which it is worn by said teeth;
   at a "dentition" instant, acquisition of at least one two-dimensional image of said teeth of said patient, referred to as "dentition image";
   2') if a determination of comparable dental and appliance attributes relative to the shape of a tooth represented on the at least one dentition image and relative to the shape of the orthodontic appliance on the at least one appliance image, respectively, is not possible from said at least one appliance image and from said at least one dentition image, respectively, conversion of at least one image chosen from the at least one appliance image and the at least one dentition image so that said at least one appliance image be compatible with said at least one dentition image;
   for each of a plurality of teeth represented on the at least one dentition and appliance images:
   3') determination of said dental and appliance attributes, the dental and appliance attributes at step 3') being:
      an outline of the tooth and of the orthodontic appliance on the dentition and appliance images respectively, or
      a surface of the tooth and of the orthodontic appliance, respectively, determined from a plurality of dentition images and from a plurality of appliance images, respectively;
   4') comparison of the dental and appliance attributes, followed by determination of at least one score according to said comparison, said step 4') comprising the following steps:
      for each of a plurality of teeth for which the dental and appliance attributes have been determined;
      i) determination of a distance between the dental and appliance attributes;
      ii) determination of a distance threshold;
      iii) for each of said teeth, determination of a distance score dependent on
         the distance between the dental and appliance attributes, and
         the distance threshold;
   at least one image chosen from of said at least one appliance image and said at least one dentition image being acquired with a mobile phone by the patient or another person.

2. The method according to claim 1, in which the appliance and dentition instants are simultaneous.

3. The method according to claim 1, in which the appliance instant and the dentition instant are separated by a time interval greater than 4 days, 1 week and less than 6 months.

4. The method as claimed in claim 1, comprising, after step 4'), the following step:
   5) comparison of the score against an acceptability threshold and emission of information according to the result of the comparison, said information being sent to a mobile phone of the patient and/or to a dental care professional.

5. The method as claimed in claim 4, wherein the acceptability threshold is parametrized by a dental care professional according to the patient's teeth configuration and/or the orthodontic appliance and/or the orthodontic treatment.

6. The method according to claim 4, said information indicating
   whether said orthodontic appliance has come off said tooth, and/or
   whether said orthodontic appliance has changed of shape between the dental instant and the appliance instant, and/or
   whether said orthodontic appliance correctly matches a surface of a tooth.

7. The method as claimed in claim 1, in which, at steps 3') and 4'), to check whether an orthodontic appliance has come off a tooth, or to check whether a shape of said orthodontic appliance has changed,
   the appliance instant and the dentition instant are separated by a time interval greater than 4 days and less than 6 months,
   the appliance attribute is an outline or a surface of said orthodontic appliance, the dental attribute is an outline or a surface of the tooth, respectively,
   the score measures a difference of positions or a difference of area between the appliance attribute and the dental attribute.

8. The method according to claim 1, wherein the orthodontic appliance is chosen among
   an aligner,
   a part which is rigidly fixed on a tooth and chosen among
      an attachment fixed on a tooth to be interposed between said tooth and an aligner in the service position,
      a button fixed on a tooth for an attachment of an elastic band,
      a bracket fixed on a tooth for an attachment of a metallic wire,
   a spring,
   a temporary anchorage device,
   a palatal expander appliance.

9. The method according to claim 1, wherein the appliance and dentition images are extraoral photographs or extracted from an extraoral film.

10. The method as claimed in claim 1, in which, at step 2'), said conversion is achieved if said at least one appliance image is not compatible with said at least one dentition image, an appliance image being "compatible" with a dentition image if the outlines of the teeth represented on the appliance image are superposable on the outlines of said teeth on the dentition image.

11. The method as claimed in claim 10, in which the step 2') comprises the following steps:
   (a') prior to step 1'), creation of a digital three-dimensional model of at least part of a dental arch bearing said teeth, or "initial reference model" and, for each tooth of the initial reference model, definition of a digital three-dimensional reference model of said tooth, or "tooth model";

(b') modification of the initial reference model by moving the tooth models until a final reference model compatible with the dentition image is obtained;
(c') search for a two-dimensional view of the final reference model that is compatible with the appliance image;
(d') conversion of the dentition image into said view.

12. The method as claimed in claim 10, in which the step 2') comprises the following steps:
(a') prior to the acquisition of the at least one appliance image, creation of a digital three-dimensional model of at least part of a dental arch bearing said teeth, or "initial reference model" and, for each tooth of the initial reference model, definition of a digital three-dimensional reference model of said tooth, or "enriched tooth model", any orthodontic appliance fixed on a tooth being part of the enriched tooth model of said tooth,
(b') modification of the initial reference model by moving the enriched tooth models until a final reference model compatible with the appliance image is obtained;
(c') search for a two-dimensional view of the final reference model that is compatible with the dentition image;
(d') conversion of the appliance image into said view.

13. The method as claimed in claim 1, in which the distances are measured in pixels.

14. The method as claimed in claim 1, in which, in step ii), the distance threshold is dependent on the smallest of the distances determined in step i).

15. The method as claimed in claim 1, in which, at step 3'), the dental and appliance attributes are determined, by means of at least one artificial neural network, from the at least one dentition image and from the at least one appliance image, respectively.

16. The method as claimed in claim 15, in which the same artificial neural network(s) is/are used to determine both dental attributes and appliance attributes.

17. The method as claimed in claim 15, in which, at step 2'), no conversion is achieved.

* * * * *